United States Patent
Caselnova

(10) Patent No.: US 7,806,841 B2
(45) Date of Patent: Oct. 5, 2010

(54) NON-AMBULATORY THERMOTHERAPY DEVICE FOR HEAT AND COLD THERAPY OF THE FOOT/ANKLE COMPLEX AND HAND/WRIST COMPLEX

(76) Inventor: Ronald J Caselnova, 83 Evelyn Pl., Staten Island, NY (US) 10305

( * ) Notice: Subject to any disclaimer, the term of this patent is extended or adjusted under 35 U.S.C. 154(b) by 137 days.

(21) Appl. No.: 11/981,045

(22) Filed: Oct. 31, 2007

(65) Prior Publication Data

US 2008/0091131 A1 Apr. 17, 2008

Related U.S. Application Data

(63) Continuation-in-part of application No. 10/438,730, filed on May 16, 2003, now abandoned, which is a continuation-in-part of application No. 09/862,227, filed on May 22, 2001, now abandoned.

(60) Provisional application No. 60/207,753, filed on May 30, 2000.

(51) Int. Cl.
*A61F 5/00* (2006.01)
*A61F 7/00* (2006.01)

(52) U.S. Cl. ................ 602/2; 602/14; 602/21; 602/27; 602/64; 602/65; 607/96; 607/111

(58) Field of Classification Search ............ 602/14, 602/23, 27, 30, 60–62, 65, 66, 2, 20–22, 602/64; 607/96, 104, 108, 111, 112, 99, 607/144, 145, 152, 149; 36/43, 141, 2.6; 601/15, 22, 28, 40, DIG. 1, DIG. 17; 2/16, 2/20, 159, 167

See application file for complete search history.

(56) References Cited

U.S. PATENT DOCUMENTS

| | | | | |
|---|---|---|---|---|
| 4,471,538 A * | 9/1984 | Pomeranz et al. | .............. | 36/28 |
| 4,701,963 A * | 10/1987 | Overton | ..................... | 2/161.1 |
| 4,958,635 A * | 9/1990 | Roberts | ..................... | 607/114 |
| 5,027,801 A * | 7/1991 | Grim | ........................... | 602/16 |
| 5,409,500 A * | 4/1995 | Dyrek | ........................ | 607/111 |
| 5,551,173 A * | 9/1996 | Chambers | ..................... | 36/44 |
| 5,591,221 A * | 1/1997 | Owens | ........................ | 607/111 |
| 5,607,749 A * | 3/1997 | Strumor | ..................... | 428/156 |
| 5,921,243 A * | 7/1999 | Shakoor | ..................... | 128/882 |
| 6,117,119 A * | 9/2000 | Gould | ........................ | 604/290 |

* cited by examiner

*Primary Examiner*—Patricia M Bianco
*Assistant Examiner*—Keri J Nicholson
(74) *Attorney, Agent, or Firm*—Adams & Wilks

(57) ABSTRACT

A non-ambulatory thermotherapy device for contacting and applying hot or cold therapy to a treatment area of a user of the non-ambulatory thermotherapy device. The device has at least one pad made of a pliable single piece of gel material for contacting a part of the user's treatment area and for undergoing selective heating or cooling to specific temperatures to selectively apply hot or cold therapy, respectively, to the part of the user's treatment area. The pad has opposite main surfaces and a plurality of bumps extending from one of the main surfaces for increasing a surface contact between the gel material and irregularly shaped contours of the part of the user's treatment area during application of hot or cold therapy to the part of the user's treatment area.

5 Claims, 18 Drawing Sheets

NON-AMBULATORY THERMOTHERAPY DEVICE FOR HEAT AND COLD THERAPY OF THE FOOT/ANKLE COMPLEX AND HAND/WRIST COMPLEX

CROSS-REFERENCE TO RELATED APPLICATIONS

This application is a continuation-in-part of application Ser. No. 10/438,730 filed May 16, 2003 now abandoned, for A Thermal Pad and Boot Designed for Applying Hot or Cold Treatment which was a continuation-in-part of application Ser. No. 09/862,227, filed May 22, 2001 for Therapeutic Boot Having Heat Retaining Protuberances (now abandoned), and provisional application Ser. No. 60/207,753, filed May 30, 2000.

BACKGROUND OF THE INVENTION

1. Field of the Invention

This invention relates to a non-ambulatory thermotherapy device comprising a thermal pad and an enclosure containing the thermal pad. The thermal pad consists of solid, pliable gel and bumps disposed throughout the entire surface of the thermal gel pad. One embodiment of the thermotherapy device is a Thermo Therapy Boot (marketed under the trademark THERMABOOT®) comprising two (2) thermal gel pads, one pad for the sole of the boot, and one pad for the body of the boot. When the two pads are sewn in their respective enclosures, the enclosures are then sewn together to form the finished boot. Specifically, the bumps are raised protuberances or nodules emanating from the gel pad itself. Therefore, the gel pad and the bumps or nodules (marketed under the trademark THERMABUMP®) are one in the same unit. The bumps or nodules are designed to help improve the surface contact with the irregularly shaped boney contours which naturally occur anatomically along the foot and ankle complex.

One model of the thermotherapy device is a boot (thermotherapy boot) designed to fit either left or right foot/ankle complex. The thermotherapy boot is manufactured in two or more sizes.

Another embodiment of the thermotherapy device is a glove (thermotherapy glove) that is designed to be used on either the left or right hand/wrist complex. The thermotherapy glove is made in a variety of sizes, also excluding the structural considerations that would be necessary for gloves which are worn for work or for one's personal attire. The thermotherapy glove continues 3" to 4" above the wrist and is secured with one VELCRO® (hook and loop fastener) strap around the distal end of the glove. The thermotherapy glove may also be designed with a second strap around the dorsal/palmar aspect of the hand. Smaller straps that are located over the knuckles or finger joints are also a considered a design of this embodiment. The thermotherapy glove also uses the THERMABUMP® design to improve surface contact between the irregularly shaped contours of the hand/wrist complex, as well as the fingers. The thermotherapy glove is used as opposed to a mitt design (prior art) in order to provide separate finger compartments for improved individualized treatment of finger injuries. The collateral swelling and soreness that normally accompany most musculoskeletal injuries will receive treatment as well as the injury site itself. The THERMABUMP® design of the thermotherapy device (boot and glove) may also be modified in shape and size for use in veterinary medicine, where heat and cold therapy is required and appropriate.

2. Background Information

The most prevalent conditions seen in podiatric practice are heel pain/plantar fasciitis, foot injury, arthritis of toes, flat fleet or fallen arches, bone spurs, hammertoes, warts or infection. A large number of these conditions require as part of the treatment regimen application of hot/cold therapy. Currently, it is extremely difficult for an individual in need of hot or cold treatment to the foot to find a thermal boot that would be suitable for effectively reducing swelling or pain to reduce inflammation and/or induce healing. The devices currently sold on the market and described in prior art, such as the gel filled mitt for hand injuries or the bead filled boot for heat therapy have several disadvantages, for example, they are unsuitable for creating temperature changes rapidly and for prolonged periods, to provide relief or they are unsuitable to be applied to hard to reach affected areas.

There is need for a thermal boot device that can effectively apply heat or cold treatments throughout the foot and/or the affected part of the foot. Hot and cold therapy devices have been subject of earlier patents, for example, U.S. Pat. No. 5,027,801, issued to Grim, discloses an orthopedic gel pad assembly including a layer of gel, a backing layer extending across the rear of the gel, and an orthopedic support means for holding the gel pad assembly against the injured body part of the user. This gel assembly is weight bearing and would not be suitable for use in the foot because in the foot, the gel pad would be bulky and difficult to keep in place, and the thermal pad would not reach difficult to reach structures in the foot.

U.S. Pat. No. 5,921,243 issued to Shakoor, describes a device for applying heat or cold therapy to a human foot having a plantar and a dorsum. The device is made of a flexible material that can wrap around the plantar and the dorsum of the foot, and the device has one pouch filled with a liquid located in the plantar region and a second liquid filled pouch located in the dorsum. The liquid in each of the pouches is used to apply heat or cold to the foot. Shakoor does not describe or suggest in any way that the liquid should be filled in a plurality of bumps, nipples or mini-pouches. The disadvantages of the Shakoor device are that liquid filled pouches in flexible material do not reach the toes, and the flat liquid filled pouches do not engage or come into contact with curves of the foot caused by bony protuberances of irregularly shaped bones in the foot such as navicular and metatarsal heads. This creates the problem of inadequate heat or cold exchange.

U.S. Pat. No. 3,595,244 issued to Kugler describes a foot-massaging sandal of flexible construction so that the toe portion may bend during walking, and the foot-contacting surface has irregularly disposed ridges which effect massaging action on the plantar surface of the foot. The disadvantage of this device is that it is constructed for massaging using ridges of various widths, heights and spacing but are solid and made of polyvinyl chloride or polyethylene.

Moreover, the device is designed so that the ridges cannot be placed over the first and fifth metatarsal heads to avoid painful massage of corns and calluses. Thus this device teaches away from the use of ridges or thermal bumps all over the foot region, or other areas in need for hot or cold therapy.

U.S. Pat. No. 5,607,749 issued to Strumor describes an acupressure massaging system including an array of spaced flexible and collapsible nipples extending vertically from the upper surface of a platform. The platform has air flow and air channels. The nipples have a collapsible accordion type structure, so that compression and movement of nipples creates a re-circulation or airflow effect through air flow channels and air flow holes to prevent suction and promote free movement of the nipples to exert an acupressure massaging counterforce on contacting surfaces.

There are other devices currently sold on the market, for example, the gel filled mitt used for hand injuries (having no thermal bumps but a smooth surface) and a boot for heat therapy, using beads to retain heat. However, these models also suffer from some of the disadvantages described above.

Accordingly, the present invention overcomes the aforementioned disadvantages and is directed to a thermotherapy device having a plurality of thermal bumps designed to enable improved penetration of heat or cold to bring relief to areas requiring treatment (treatment area). The invention provides specific products suitable for hot/cold therapy of foot conditions, as well as products that are developed for applying heat/cold therapy to the elbow, knee, ankle, neck, hand, wrist, shoulder, back, lumbar region, sinuses, temporo mandibular joint, head and pressure point areas where bed sores develop.

Many foot and ankle conditions such as sprains; strains; plantar fascitis; post surgical and certain fractures which are treated by rehabilitation professionals and physicians will, at some point, require heat and/or cold therapy as part of their rehabilitation protocol. The thermotherapy device of the present invention is not only appropriate for professional clinics, it is also easy and convenient enough for an individual to use at home.

Circulation is most difficult to and from the distal areas of the extremities. In this case, the foot and ankle or the hands and wrists. A boot is necessary for heat/cold therapy when treating ankle/foot injuries for two basic reasons:

(1) Swelling and inflammation will encompass healthy tissues collateral to the injury site; therefore, coverage of the foot/ankle complex, completely, ensures a superior heat cold therapy treatment; and (2) As mentioned earlier, the foot and ankle are the most difficult areas of the human body to deliver blood to, and remove metabolites (waste products) from. Keep in mind, blood carrying nutrients and oxygen are an important part of the healing process. The boot and glove designs of the present invention provide necessary and very effective means of promoting circulation through heat/cold therapy. Another convenience and an important consideration of the thermotherapy device of the invention is that the boot is designed so that one boot can be used on either the left or right foot and ankle.

The thermotherapy device of the present invention optionally requires a means of fastening. In the thermotherapy boot, there are three adjustable VELCRO® fasteners (as defined herein): one around the ankle; one at the forefoot; and one at the proximal aspect of the toes (metatarsal/phalangeal/joints). The straps are used only to provide the wearer with a snugger or looser surface contact between the foot and ankle against the boot. The forefoot and metatarsal straps hook or fasten on the outside, or bottom of the boot. This is designed as a built-in reminder to the wearer that thermotherapy boot is not designed or intended for walking, weight bearing, or any type of shock absorption. A person with a fracture or post-surgical situation should not weight bear, as this may disrupt the healing process.

The thermotherapy device of the present invention is designed for heat or cold therapy. This is better demonstrated through two illustrations included with this application. A person receiving heat/or cold therapy to the foot/ankle will either lie down with the affected leg raised just above the heart line, or seated comfortably. A reclined or semi-reclined position will best promote both lymphatic and blood circulation.

Since the thermotherapy device of the present invention does not use sealed chambers with liquids encapsulated within, there is no chance of leaking or drying up. The thermotherapy device can continue to function even if it is torn. Thus, it adds a very important cost-effective feature to the device.

Although there are existing Square Packs as well as specialty shaped heat/cold packs that are available, as stated earlier, it is important to cover the entire foot/ankle complex when treating the area with heat/cold therapies. The thermotherapy device of the present invention provides consistent applications through complete coverage of the areas every time it is used: covering only part of these areas is not thorough enough. For this reason, there is a need for a thermotherapy boot that can effectively apply heat or cold treatments to the foot/ankle complex.

Heat and cold therapy devices, amongst other embodiments, have been the subjects of earlier patents: (U.S. Pat. No. 5,921,243 Shakour); (U.S. Pat. No. 5,027,801—Grim). Grim's is a weight-bearing device. Shakour's device uses liquid pouches that can't match the more cost effective method used by the thermotherapy device of the present invention. Other embodiments include: (U.S. Pat. No. 3,595,244—Kugler) which is a foot massaging sandal; (U.S. Pat. No. 5,607,749—Strumor) an acupressure massaging system, both come in pairs and are for walking and designed with shock absorption. In summary, while these devices are fine, they teach an entirely different art and focus on entirely different matters.

In addition, (U.S. Pat. No. 5,551,173—Chambers)—Chambers' device is reversible insole with a reflexology chart included. U.S. Pat. No. 4,471,538—Pomeranz, is a shock absorbing device using Rheopexic fluid. U.S. Pat. No. 5,553,399 is another art that teaches shock absorption as well as depending on one's own body heat to protect against cold weather conditions.

None of the above-mentioned devices in the prior art claim therapeutic temperature retaining properties. In addition, these applications involve only body heat exchange. They teach ambulation and shock absorption using Rheopexic fluid.

In contrast, the thermotherapy device of the present invention exhibits heat and cold retaining properties, as well as defines the parameters of heat and cold therapy in order to further substantiate the validity of this device. With regard to heating or cooling, the thermotherapy device of the present invention will remain soft and pliable even in temperatures as low as −20° F. Many other devices for heat and cold therapy will become stiff and or brittle when left in a freezer for a prolonged period of time. This characteristic would not be appropriate or comfortable for this very specific application and use. The thermotherapy device of the present invention can be prepared to provide 20 to 30 minutes of cold therapy after 2 to 3 hours in a person's freezer at home. The thermotherapy device can also be prepared for heat therapy by being placed in a household microwave oven (45 seconds each side—approximate times). This device can also be prepared for heat therapy when placed in a water tight container and placed in a hydrocollator (electric boiler) for about an hour. Hydrocollators are commonly used in rehabilitation clinics to heat the common square or neck silica heat packs. This versatility of preparation offers convenient choices to the user.

It is a commonly accepted fact that water temperature above 98.6° F. (body temperature) is said to be hot. Water that is about 70° to 80° F. is considered cool. In addition, water at 55° F. and below is considered cold. On this basis, the thermotherapy device of the present invention will achieve the necessary temperatures that are used to define both heat and cold therapy. When using any type of heat or cold therapy, it is necessary to prepare and monitor the wearer. The wearer must always use insulation between the skin and contact surface of the device. With regard to the thermotherapy device of the present invention, a thick sock, such as an athletic sock should be worn to provide a more comfortable, safer thermotherapy. With further consideration to heat/cold therapy, Stillwell (1972) states that a minimal time of 20 minutes is physiologically sound for the duration of a heat treatment. Lehman (1982) states that the temperature must be elevated between 40° C. and 50° C. (104° F. to 113° F.) in order to be of therapeutic value. Below 40° C., heating is considered mild. While other experts may differ somewhat on what the appropriate times and temperatures for thermotherapy are, the thermotherapy device of the present invention will achieve the necessary levels of temperature for providing therapeutic heat and cold treatments. In addition, if the temperature increases too slowly, then the amount of heat added could be balanced out by the convective effect of cooler blood, thereby causing the effective therapeutic levels to be obtained.

The thermotherapy device of the present invention uses an existing technology that will heat or cool slowly and comfortably for the wearer with safety, also a paramount consideration. Other embodiments use a form of fastening so that the wearer has stability during ambulation/weight bearing activities. The thermotherapy device of the present invention uses three fastener straps that may be VELCRO® or another type of fastener as well. The function of the three adjustable straps is to increase or decrease surface contact between the foot and ankle against the boot. Explaining further into the background of the present invention, the polymer gel initially is a liquid substance which is poured into a mold. The mold is made of oak or plywood and measures 26 inches in length and 12 inches wide. There are two shapes carved into the mold. The two shapes are the sole and body of the device. Both of these shapes have dimples or concavities further tooled throughout the entire surfaces of the two shapes. These dimples or concavities measure ½" to ¾" deep. A scrim is placed on the back of the sole and body shapes while they are setting in the mold. The scrims are ⅛" or less thick. They are made of cloth and provide a means of reinforcement to protect the two gel pieces from cracking. Once the gel sets, the sole and body gel shapes are pulled from the wooden mold. The ½" to ¾" dimples or concavities will form the soft dimples or nodules providing the THERMABUMP® design. The THERMABUMP® design provides a superior contact between the dorsal and plantar aspects of the metatarsal heads; the dorsal and plantar aspects of the tarsal bones; and the medial and lateral malleoli, which are the two boney protuberances we usually refer to as the ankle. The THERMABUMP® design is soft and pliable enough so that it will not cause compromise or cause discomfort to the wearer.

There are other devices which, we maintain, have certain disadvantages such as liquid or gel filled chambers that can leak. There are ice packs that, when frozen, become hard and brittle over a period of time. There are other devices which provide only partial coverage of the foot and ankle, as well. The thermotherapy device of the present invention is specifically designed for easy and convenient use. Also, the present invention envelops the entire foot/ankle complex which ensures consistent treatment every application. In spite of these prior arts, there remains a substantial necessity for a convenient, cost effective and thorough choice for heat/cold therapy treatment of the foot/ankle complex.

SUMMARY OF INVENTION

The present invention is directed to a non-ambulatory, heat and cold thermotherapy device. The present invention is designed to provide thermotherapy only. It is not designed for ambulation, weight bearing, or shock absorption. The present invention may be used for heat or cold thermotherapy at home, or in a professional clinic, hospital, and any other physical rehabilitation setting.

The non-ambulatory thermotherapy device is designed to treat the most difficult area for blood circulation to travel to or from the foot/ankle complex.

The thermotherapy device is designed with two gel pads in the sole and body of the boot. The two gel pads are contained each within its own high performance cloth enclosure that houses each gel pad. The two enclosures are sewn together to form the thermotherapy device. The two solid, but soft, pliable gel pads are based on an existing polymer gel technology. The gel, initially in a liquid form, is poured into a wooden mold. A cloth scrim for reinforcement is placed on each of the two shapes while still setting in the mold. The gel sets to two soft, pliable solid pieces. The two gel pads are molded with dimples or nodules which are formed out of the concavities tooled along the surfaces of the two shapes that are carved into the wooden mold. The nodules or dimples measure about ½" to ¾" in depth. The two gel pieces, are pulled from the mold to reveal that the dimples or nodules are continuous along the gel pad surfaces, and are in fact, one and the same part. The nodules or dimples providing the THERMABUMP® design of the thermotherapy boot will provide a better contact surface between the irregularly shaped contours of the foot/ankle complex and the interior treatment surface.

The thermotherapy boot is designed in a generic shape and manufactured in two sizes: medium and large. One thermotherapy boot is designed to fit either the left or right foot/ankle complex.

The current invention is capable of remaining soft and pliable even at temperatures as low as −20° F. The device will also achieve the therapeutic heat temperatures of 109° C. to 113° F. The device will provide heat or cold therapy lasting between 20 and 30 minutes.

The present invention can still be used for thermotherapy even if a tear or puncture in the device should occur, without any compromise to the wearer or the therapeutic procedure.

The present invention uses three adjustable straps, measuring in 2" width each. The adjustable straps provide the wearer with a means of adjusting the degree of contact between surfaces of the wearer's foot/ankle and the treatment surfaces of the boot. The three adjustable straps are located at the fore foot, the metatarsal/phalangeal articulations, and the ankle. The adjustable straps also help negate the necessity for exact sizing, thus making this device considerably more cost effective. The present invention is designed with ample flexibility to allow for swelling or inflammation and discomfort that normally accompany conditions such as arthritis, plantar fascitis and post surgical procedures.

It is widely known, understood, and a common behavior among people who need to follow physical rehabilitation protocols that the more involved or difficult the protocol, the least likely the person will be to maintain a consistent pattern of treatment. Therefore, it is an object of the present invention to help increase patient compliance.

It is another objective of the present invention to provide improved contact and, thereby, improved thermotherapy for irregularly shaped areas of the foot/ankle complex.

It is further an objective of the present invention to provide a cost-effective mold system that is easy to manufacture.

It is another objective of the present invention to provide the user or wearer with consistent thermotherapy conditions.

It is another objective of the present invention to provide one boot device which can be comfortable and worn interchangeably on either the left or right foot/ankle complex.

It is yet another objective of the present invention to provide two generic sizes that will accommodate the majority of foot sizes that are in need of thermotherapy, without worry or concern for exact sizing to the wearer.

It is another objective of the present invention to provide a thermotherapy device that will not become hard or brittle when frozen. Because the present invention is a specialized shape, this is of paramount importance.

It is another objective of the present invention to provide a thermotherapy device for the foot/ankle complex that is easy to store.

It is a further, an objective of the present invention to provide a thermotherapy boot that can be easily prepared for heat or cold therapy in an individual's home freezer, microwave, or boiling water within a reasonable amount of time.

It is also an objective of the present invention to provide the wearer with a soft, flexible thermotherapy boot that can be comfortably worn for therapy, even in cases of swelling, sub-acute pain and inflammation.

BRIEF DESCRIPTION OF THE DRAWINGS

The advantages and features of the present invention will become readily apparent after reading the following detailed description and referencing the drawings. In the drawings, like elements are depicted by like reference numerals. In order to facilitate a fuller understanding of the present invention, reference is made of the drawings which should not be construed as limiting the present invention, but are intended to be exemplary only and, which are.

DETAILED DESCRIPTION OF THE PREFERRED EMBODIMENTS

Figure 1:
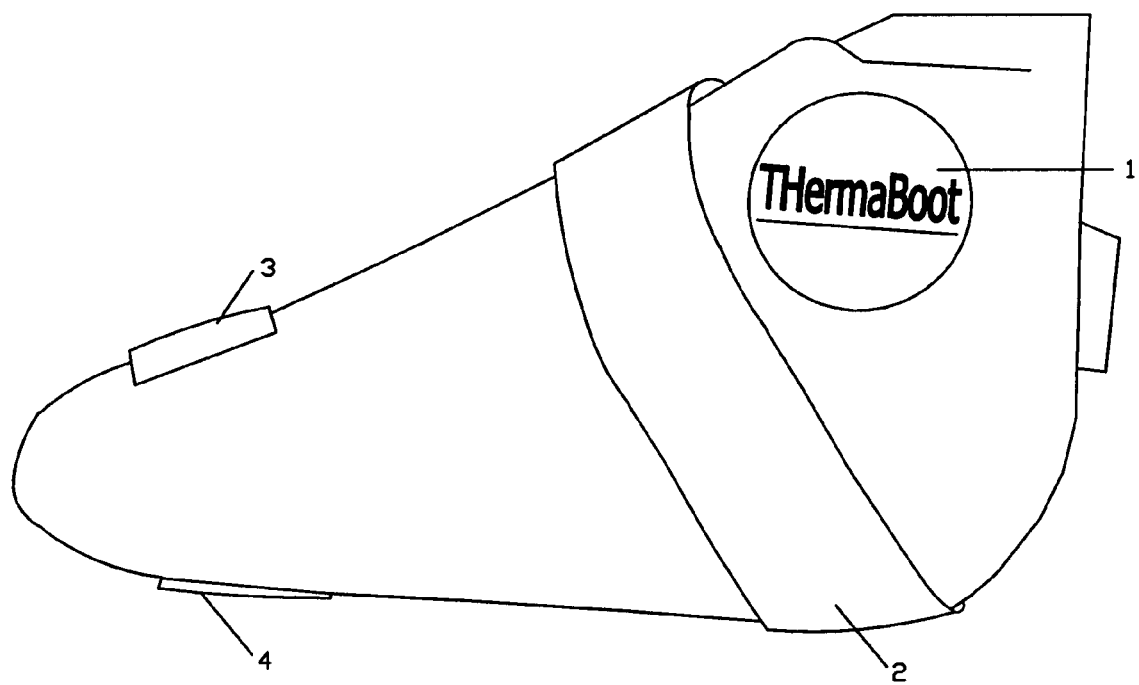
FIG. 1 is a side view of the thermotherapy device according to the present invention, showing the logo label THERMA-BOOT®, toe strap and forefoot strap. The ankle strap is not shown for a clearer view of the logo label.

FIG. 1 shows a sagittal view of the thermotherapy device. The logo label (1) is in plain view. A partial view of fore or mid-foot adjustable strap (2) and the adjustable toe strap (3) are shown. A partial view of the toe strap attachment (4) which is located on the sole of the boot is also shown. The exterior and interior enclosures of the device are made of a high performance textile known as "TEK-STRECH" which has water repellant finish added to it. This allows the boot to be cleaned with a damp cloth or household disinfectant. This textile provides the only enclosure necessary for the solid, soft gel pads.

Figure 2:
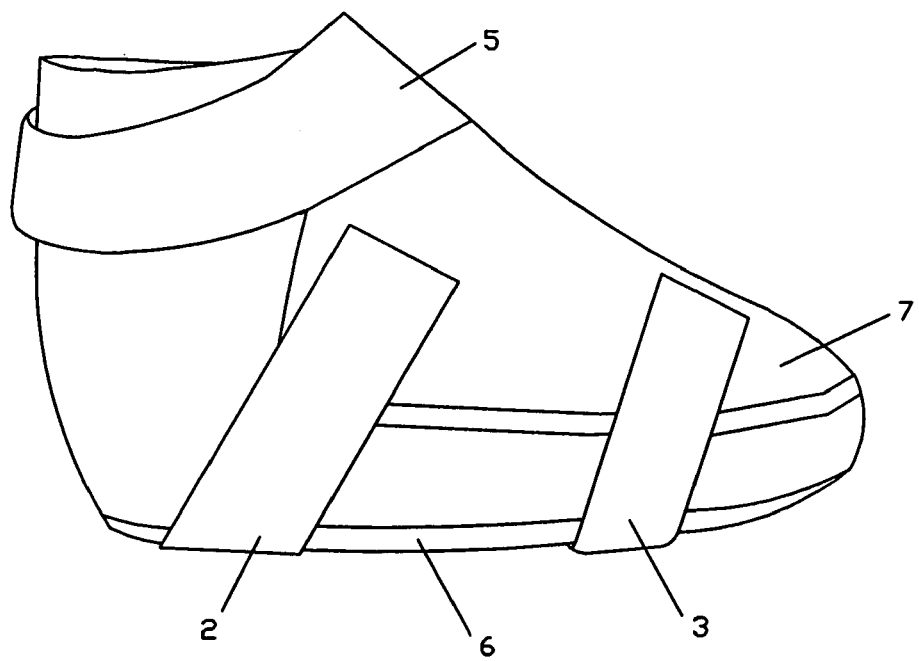
FIG. 2 is another side view showing the three adjustable straps. A. Ankle strap; B. Forefoot strap; C. Toe Strap.

FIG. 2 is another sagittal view of the thermotherapy device. This illustration shows the ankle strap (5). Also illustrated is a side view of the sole (6) of the device. The sole (6) and body (7) are soft and pliable, which provides not only easy storage, but a comfortable fit for the wearer. This feature of the device is particularly important in cases of discomfort due to inflammatory conditions such as post surgical situations, plantar fascitis and arthritis, among others.

Figure 3:
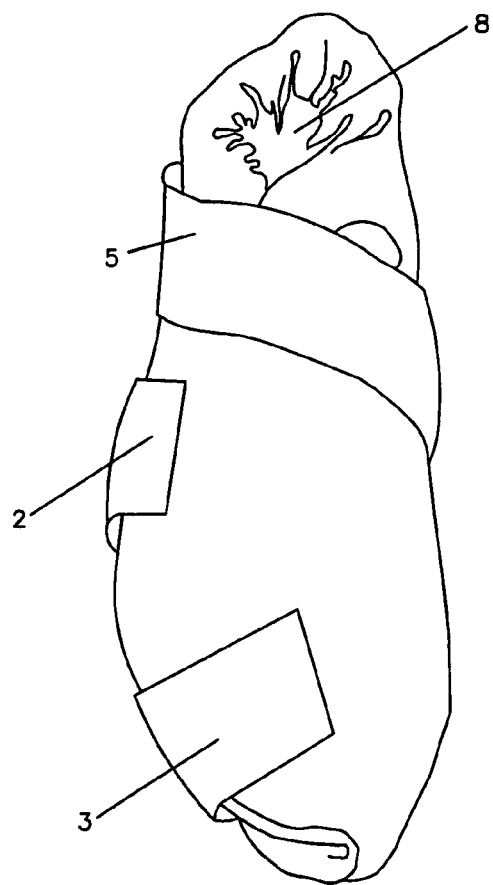
FIG. 3 shows an anterior view of the thermotherapy device, with three adjustable straps.

FIG. 3 presents an anterior view of the thermotherapy device. This illustration shows the waviness, or pliable feature of the device. Also viewed is the opening (8) which opens wider to accommodate conditions that involve swelling. A partially anterior view of the fore or midfoot strap (2) is shown. Shown also here are ankle strap (5) and the toe strap (3) as well. The thermotherapy device is designed for use by people who require heat or cold therapy for injuries, chronic painful conditions of the foot and ankle complex, and for general maintenance or care of one's foot and ankle. In order to accommodate these populations, a soft and pliable design is an important consideration.

Figure 4:
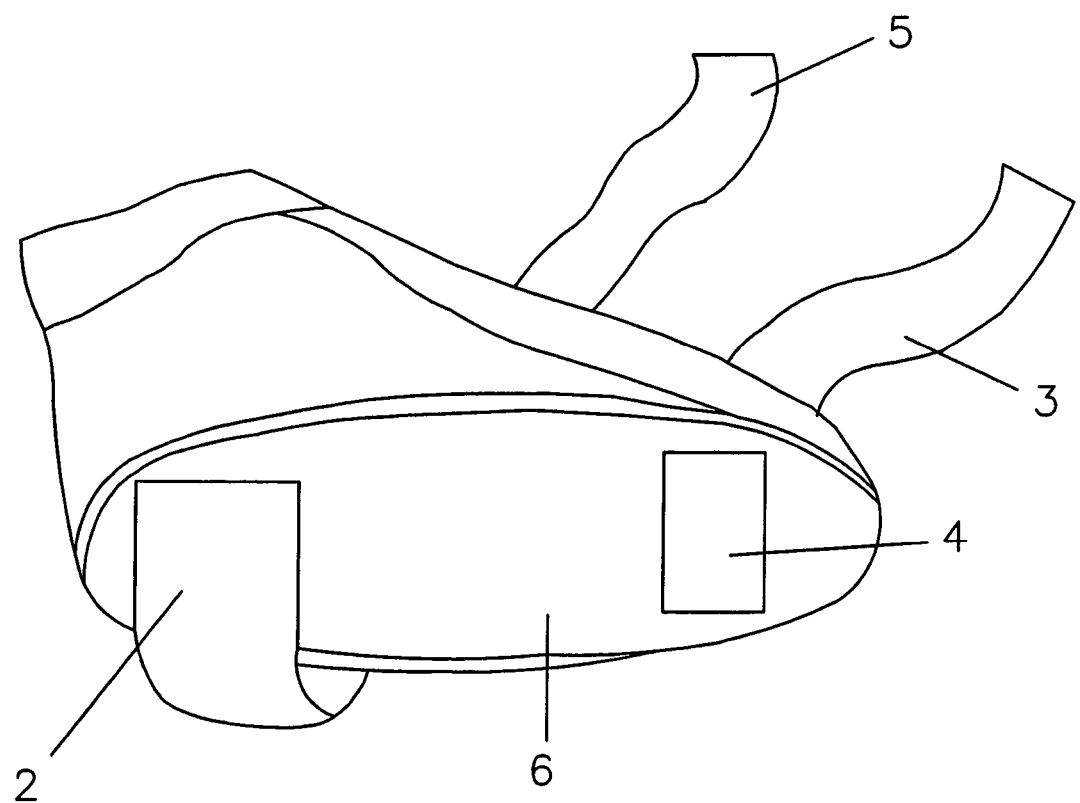
FIG. 4 shows sole and side views of the thermotherapy device.

FIG. 4 is a view of the side and bottom of the device. Note the sole (6) with the toe strap attachment (4) in full view. The fore or mid foot (2) strap is illustrated attached at the rear portion or heel of the device, located on the sole (6). The toe strap (3) and ankle strap (5) are drawn unattached.

Figure 5:
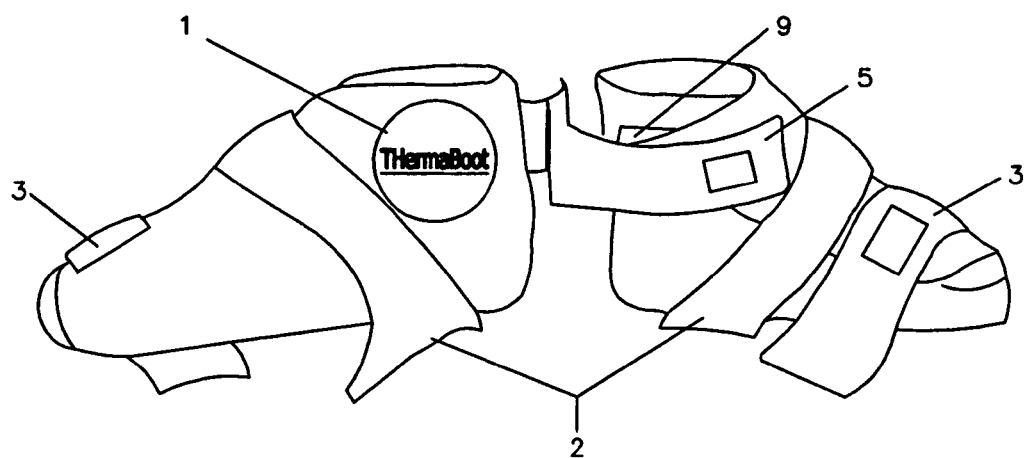
FIG. 5 shows left and right views of the thermotherapy device. Also viewed are the adjustable straps. Note that these views demonstrate that one boot is designed to fit either left or right foot/ankle complex.

FIG. 5 illustrates a left and right view of the thermotherapy device. The device is designed in two sizes, medium and large. This drawing is further meant to show the symmetrical shape, the intention is a practical one, that is one boot is all that is required to treat either the left or right foot and ankle complex. The illustration on the right shows the ankle attachment (9), partial view. In addition, other angles of the toe strap (3), mid or forefoot strap (2); and ankle strap (5) are also featured.

Figure 6:
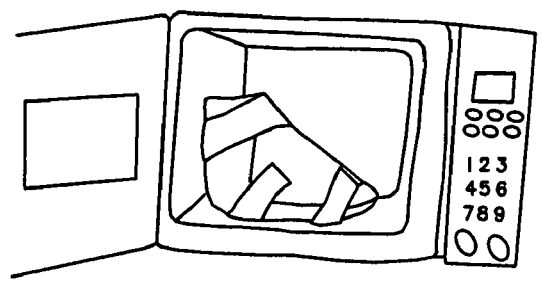
FIG. 6 shows the thermotherapy device ready for heat therapy prepared in a microwave oven.

FIG. 6 illustrates the thermotherapy device placed in a microwave oven for heat therapy preparation. Depending on the power of wattage of the microwave, the present invention can be ready for most heat therapy in about thirty (30) to sixty (60) seconds. A thick sock (not shown) such as athletic sock, may be worn for insulation. A layer of insulation is advisable with any type of heat or cold therapy, especially for elderly people or people with sensory neurological conditions.

Figure 7:
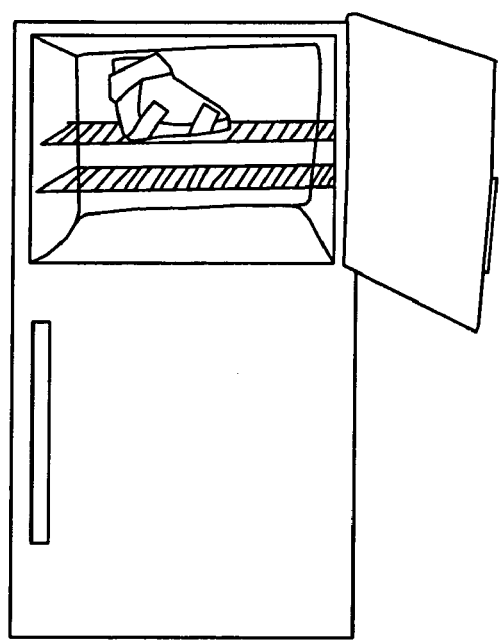
FIG. 7 shows the thermotherapy device being prepared in a household freezer for cold therapy.

FIG. 7 shows the thermotherapy device placed in a household freezer for cold therapy preparation. This takes about an hour for preparation. The device may be stored in your household freezer on an ongoing basis, because the device will not become hard or brittle, like other cold therapy devices, even in temperatures as low as −20° F.

Figure 8:
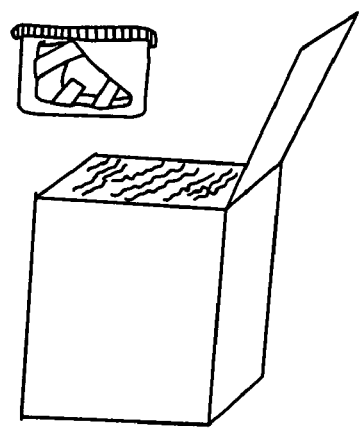
FIG. 8 shows the thermotherapy device in a water tight container, prepared to be placed in a hydrocollator (electric boiler).

FIG. 8 shows the present invention placed in a water tight container before being placed in an electric water boiler, called a hydro collator. Hydrocollators are commonly found in physical therapy clinics and other types of physical rehabilitation facilities or physicians' offices that provide thermotherapies, including spas. The device cannot be submerged in water due to the glycerin based nature of the polymer gel pad. This technology allows the thermotherapy device to provide moist heat which is more penetrating than dry heat.

Figure 9:
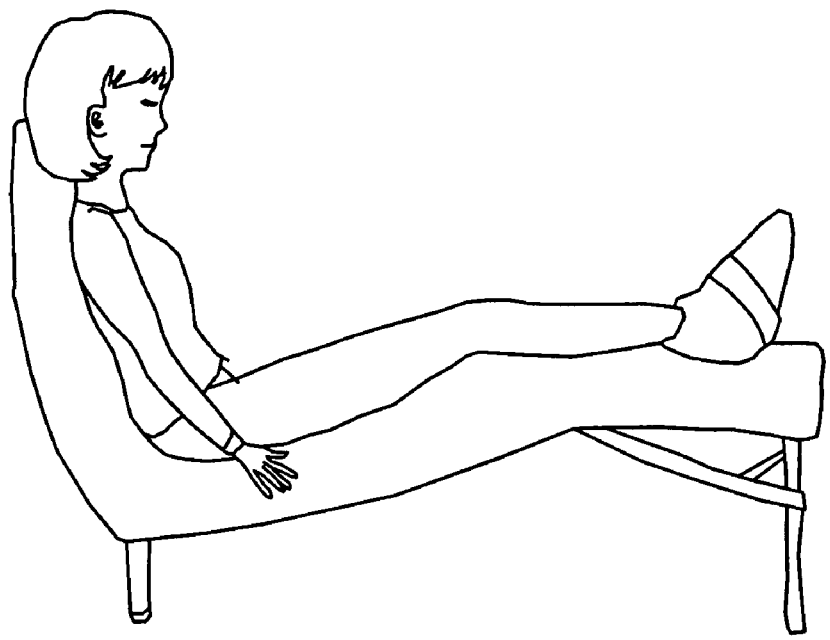
FIG. 9 shows a person using the thermotherapy device in a reclined position.

FIG. 9 illustrates the wearer in a reclined position with the wearer's leg raised at a moderate level.

Figure 10:
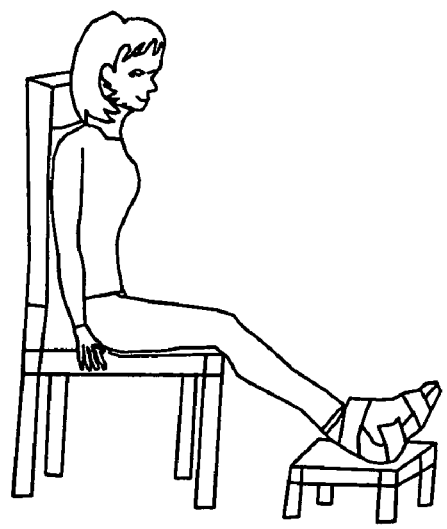
FIG. 10 shows a person in a seated position. This is an appropriate position as well and may be used by the wearer if a reclined position is not an option.

FIG. 10 illustrates the wearer seated with the foot and ankle being treated resting on a foot stool. This is an acceptable position for the therapeutic process if a reclined or semireclined position is not an option (uncomfortable to the wearer).

Figure 11:
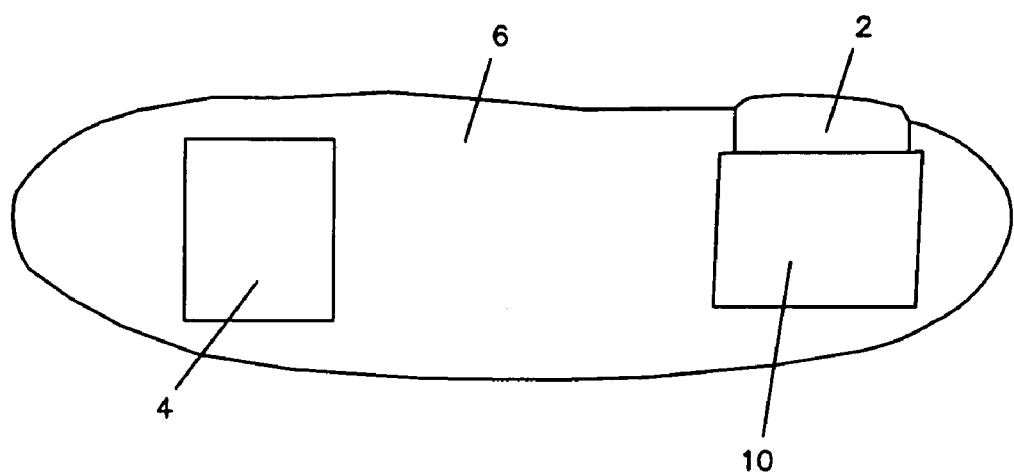
FIG. 11 is a view of both attachments for forefoot, (or midfoot) and toe strap, shown on the sole or plantar surface of the thermotherapy device.

FIG. 11 is a view of the sole (6) or plantar surface of the thermotherapy device. The forefoot, or midfoot attachment (10) is in clear view at the heel area. The toe strap attachment (4) is located on the bottom of the boot, in the front area or toe compartment. The mid or forefoot attachment (10) and toe strap attachments (4) are designed on the sole (6) of the thermotherapy device as an added reminder that the device is a non-ambulatory, non-weight bearing device. In addition, a person taking heat or cold therapy should be off his or her feet when receiving heat or cold therapy of the foot ankle. This promotes better circulatory drainage during the therapy session.

Figure 12:
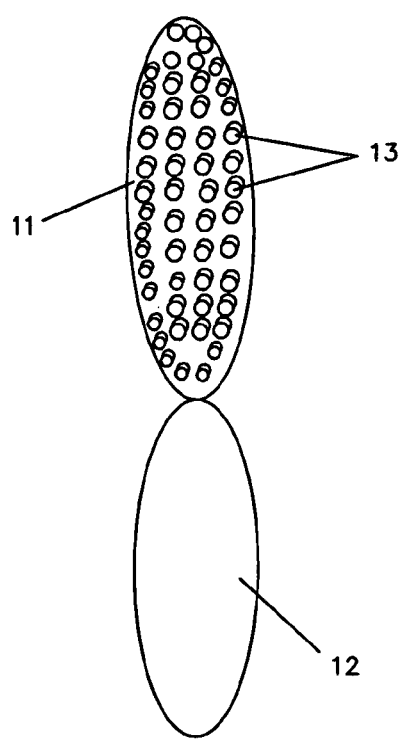
FIG. 12 shows the gel sole contact surface of the bumps exposed. The cloth enclosure is peeled back to demonstrate this view.

FIG. 12 shows the sole (6) which is made of a polymer gel pad (11). A cloth (12) enclosure is peeled back. A plurality of the bumps (13) having the THERMABUMP® design are in full view.

Figure 13:
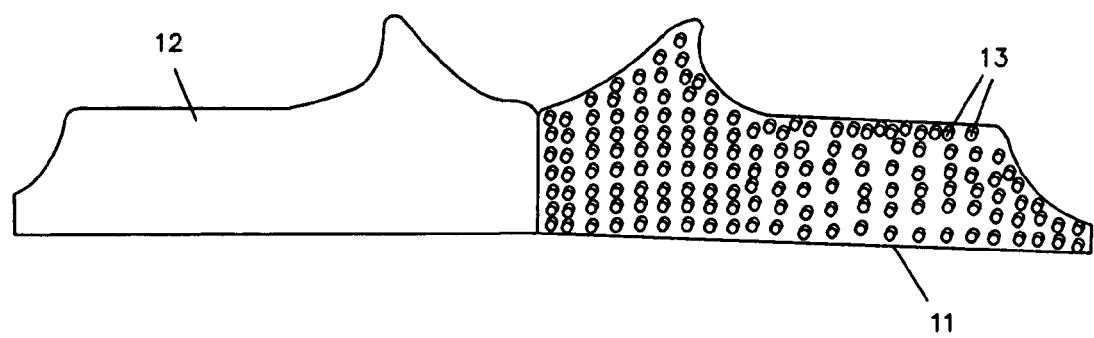
FIG. 13 shows the gel body's contact surface with its cloth enclosure peeled back to view the gel pad with the bumps.

FIG. 13 shows the gel pad (11) which is the body section (7) of the boot, its cloth (12) enclosure is peeled back. The two surfaces displayed in FIGS. 12 and 13 show the bump (13) sides, which provide the contact surfaces against the wearer's foot and ankle complex. The bumps (13) on the interior surfaces of the sole (6) and body (7) are designed to provide a better contact surface on the irregularly shaped curves and contours of the foot and ankle complex. The major areas are the metatarsal heads which articulate with the proximal phalanxes of the toes; the tarsal bones of which there are seven small bones; and the area posterior to the medial and lateral malleoli which is commonly called the ankle.

Figure 14:
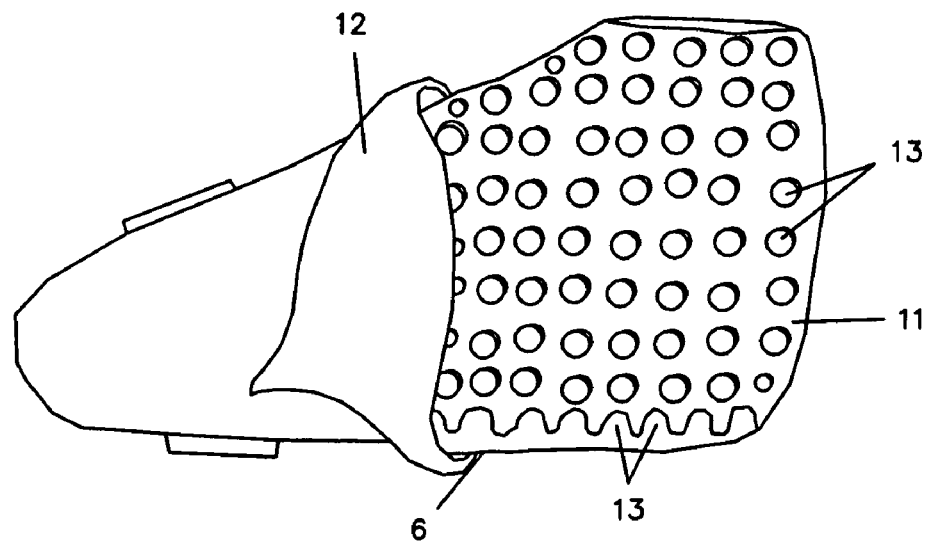
FIG. 14 shows a partially peeled back view of the body's interior bump contact surface of the device. Also viewed is a partial sagittal view or profile of the bumps that provide the contact surface of the sole.

FIG. 14 is an illustration of the cloth enclosure (12) peeled back. This is a partial view of the gel pad (11) that is the body (7) of the boot. A sagittal view of the bumps (13) on the sole (6) are also shown. The bumps (13) emanate out of sole (6) of the device.

Figure 15:
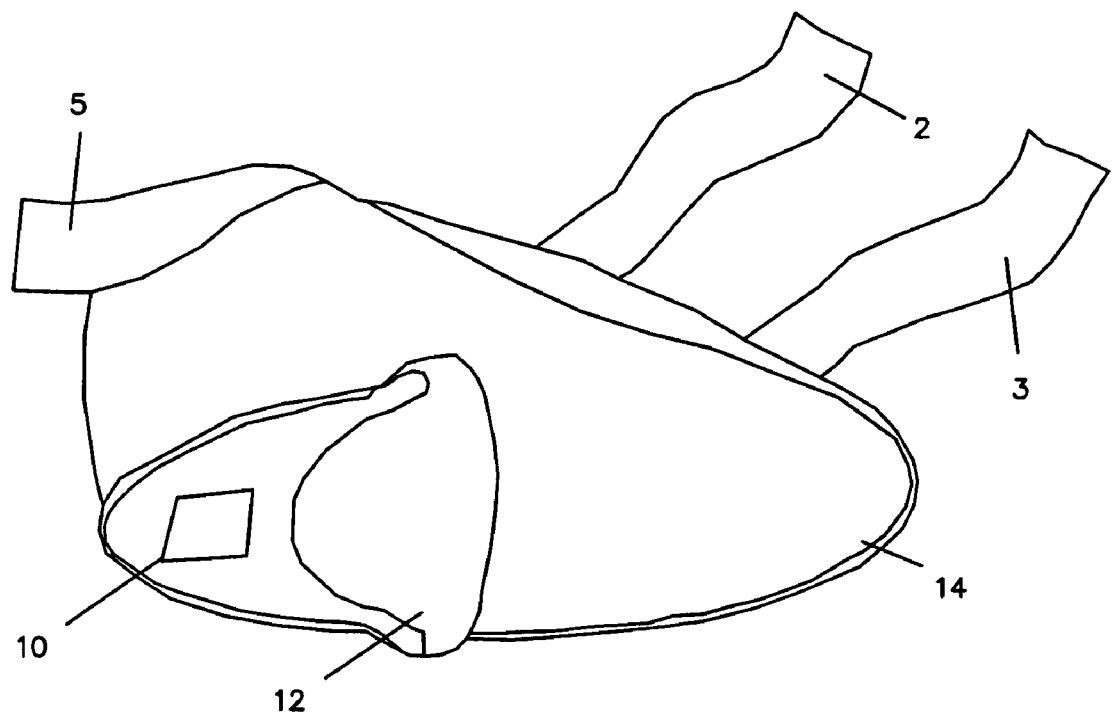
FIG. 15 shows a cloth sole enclosure peeled back, showing a partial view of the exterior aspect of the sole gel pad. The black area represents the cloth scrim which is set into the gel before it is cool. The scrim provides a practical, cost-effective support for the thermo therapeutic gel sole, and the boot body as well.

FIG. 15 shows the cloth enclosure (12) of the bottom of the sole (6) peeled back to show the cloth scrim (14) which is placed on the backside of the two gel pads (11) to provide reinforcement and protect the integrity of both shapes. The scrim (14) is about ⅛" thick. The toe strap (3) and the mid or forefoot strap (2) are in full view. The ankle strap (5) is cut away.

Figure 16:
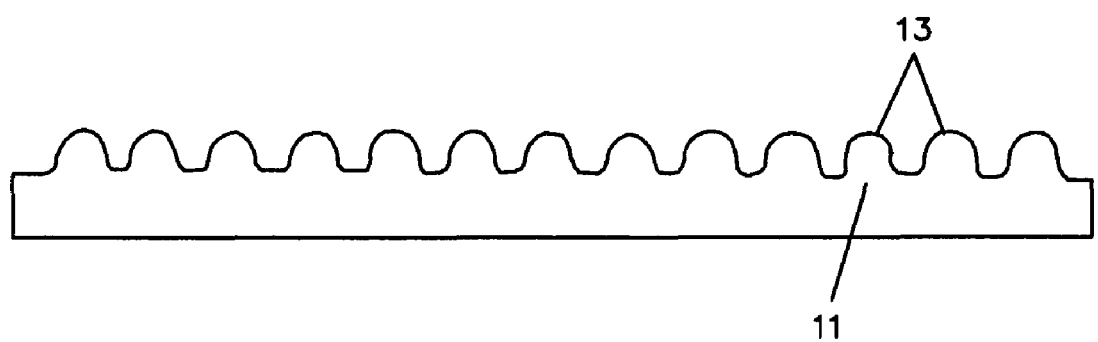
FIG. 16 is a sagittal view of a section of the finished gel pad. Note clearly, the bumps emanate from the pad, therefore making them one in the same.

FIG. 16 shows a saggital view of a section of the finished thermotherapeutic gel pad (11). The important features here are that the bumps (13) emanate from the gel pad (11) making this one piece. These are no seams, therefore, no leaks. The other feature is this makes the present invention practical as well as cost-effective.

Figure 17:
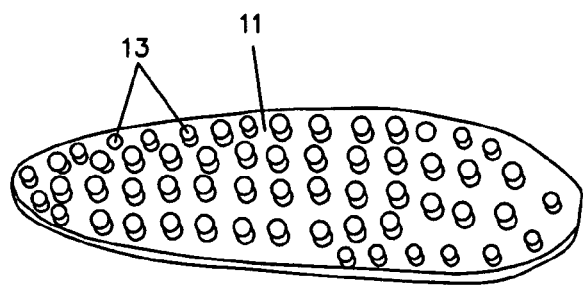
FIG. 17 shows the finished thermotherapeutic gel pad sole with the bumps fully illustrated, all one unit.

FIG. 17 illustrates a top view of the finished sole (6) which is one of the two gel pads (11), with the bumps (13) formed in one piece with the gel pad (11). The bumps (13) cover the entire interior or contact surface. They are soft and pliable, and comfortable for the wearer.

Figure 18:
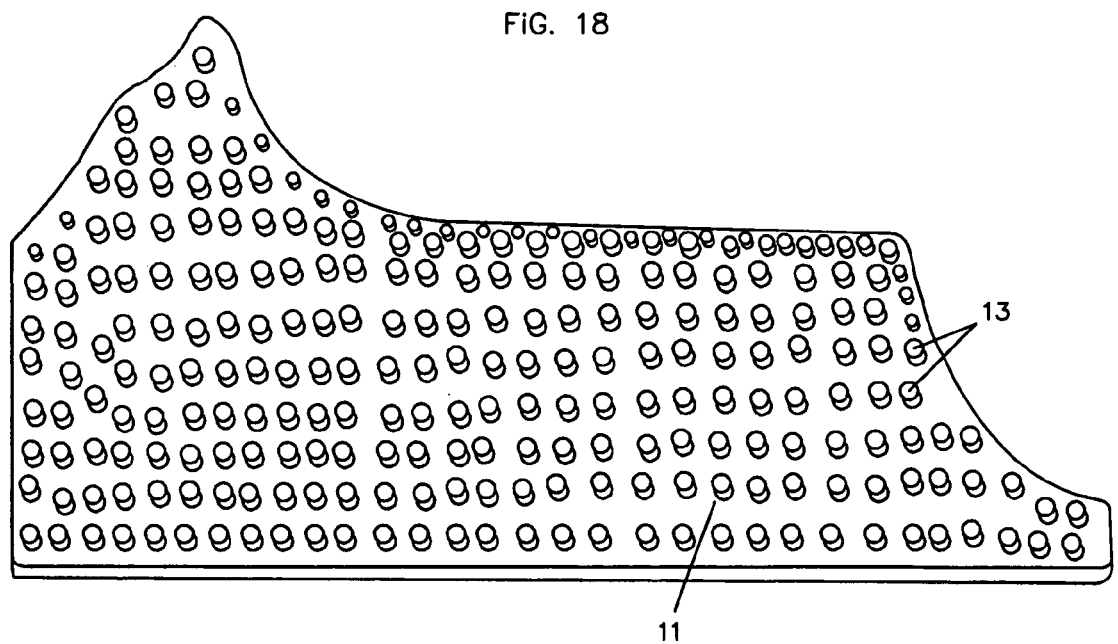
FIG. 18 is top view of the thermotherapeutic gel pad body with the bumps fully illustrated.

FIG. 18 is a top view of the finished gel pad (11) corresponding to the body (7). It is also a soft and pliable thermotherapeutic polymer based gel pad. The body (7) section of the two gel pads (11) provides heat or cold therapy to the rest of the wearers foot and ankle complex. The interior or contact surface of the body gel pad (11) also is entirely covered with the nodules or bumps (13). This section covers the dorsal lateral aspects of the foot and ankle complex; the lateral posterior aspects of the heel, and the entire ankle.

Figure 19:
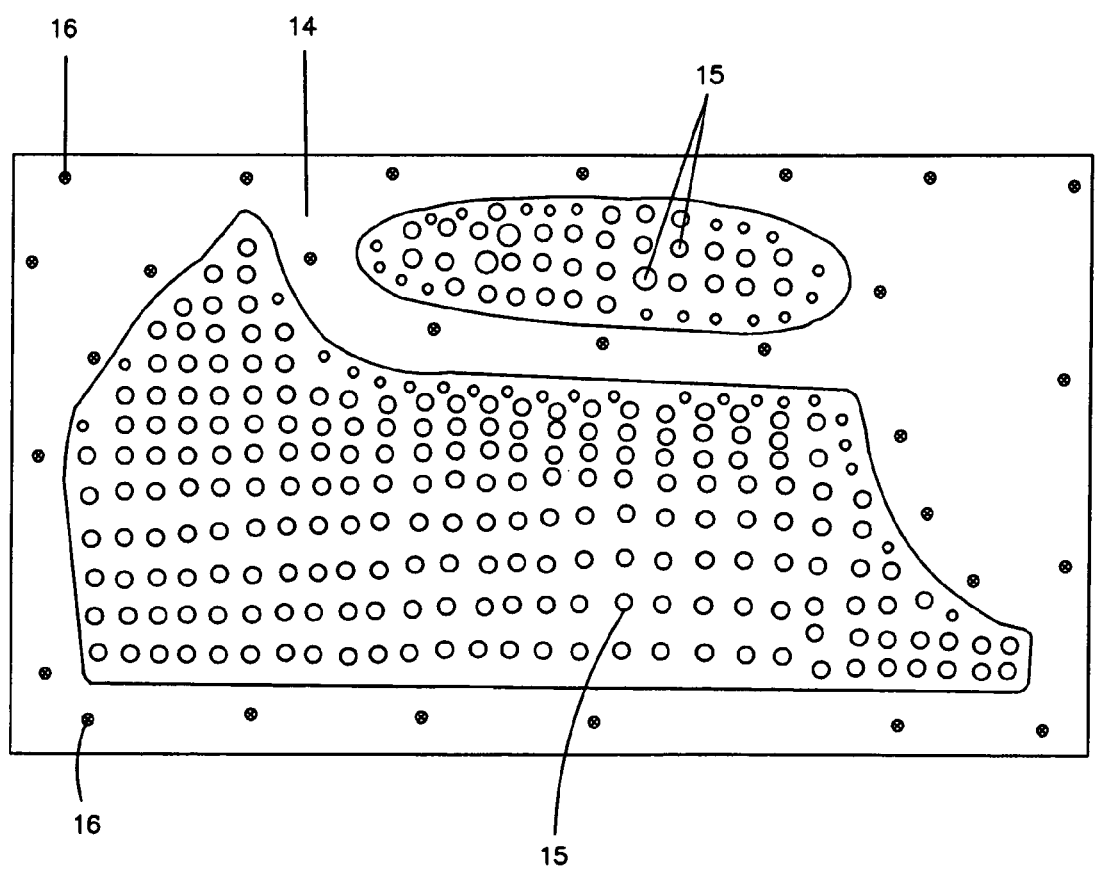
FIG. 19 illustrates the mold for the thermotherapy boot, including a top view of the sole, body and concavities.

FIG. 19 is a top view of the mold (14). The dimples or concavities (15) are tooled into the two shapes. The dimples or concavities are each about ½" to ¾" deep. This type of mold (14) is significantly more cost effective than certain other mold technologies, i.e., injection molding. The mold (14) can be made of oak or a high grade plywood. Other harder woods may also be left up to the consideration of the manufacturer. The mold (14) is currently made in two sizes: medium and large. The mold is fastened together with screws (16). The mold (14) measures about 13" wide and 26" deep. The base of the gel pads (11) is about ⅜" thick. The bumps (13) emanate about ½" to ¾" above the gel pad. Preferably, the bumps are ½"-1" in diameter and depth.

Figure 20:
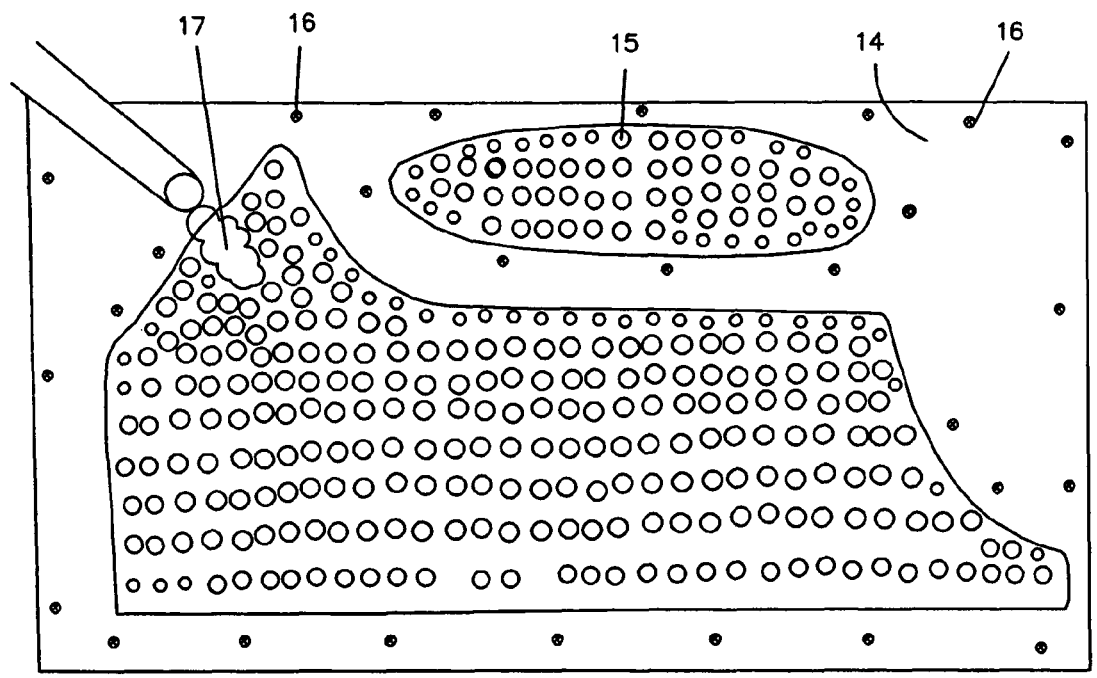
FIG. 20 illustrates a top view of the mold. At left side is a view of the gel, in its initially liquid form, being poured into the mold.

FIG. 20. is a top view of the liquid form (17) of the polymer based thermo-therapeutic gel being poured into one of the molds (14) to set. This is illustrated at the top left hand side of the illustration. The gel pad (11) body (7) section of the boot is being poured first. The liquid gel (17) takes the shape of the concavities (15) which form the bumps (13). This is how the bump (13) system is formed for the sole (6) which is also a gel pad (11) section as well. Again, there are no liquid filled chambers or enclosures. There are significantly less parts to manufacture, making the present invention less labor intensive than some existing devices. Stitching or heat sealing are not used, which negates the possibility of leaks or drying out as with liquid devices and methods. The thermal technology employed in the present invention will remain soft and pliable in temperatures as low as −20° F. The mold (14) is cost effective for manufacturing; and, the present invention cost-effective for the consumer as well as convenient for storage.

Figure 21:
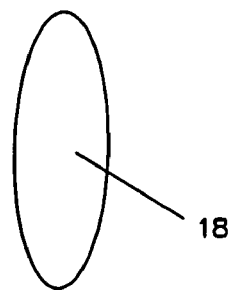
FIG. 21 is a top view of the two cloth scrim shapes which provide reinforcement for the sole and body gel pads.
Figure 21:
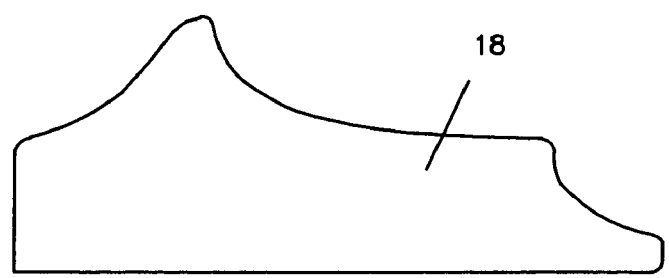

FIG. 21 is an illustration of the two (2) scrim (18) sections. They are about ⅛" or a little less in thickness, and they are made of a cloth-like material. The scrims (18), shaped like the sole (6) and the body (7) gel pad (11) are placed on the top of the mold (14) directly over each of the two shapes as the liquid (17) gel is setting in the mold (14). The scrims (18) serve as reinforcement or a means of support for the two thermotherapeutic gel pads (11).

Figure 22:
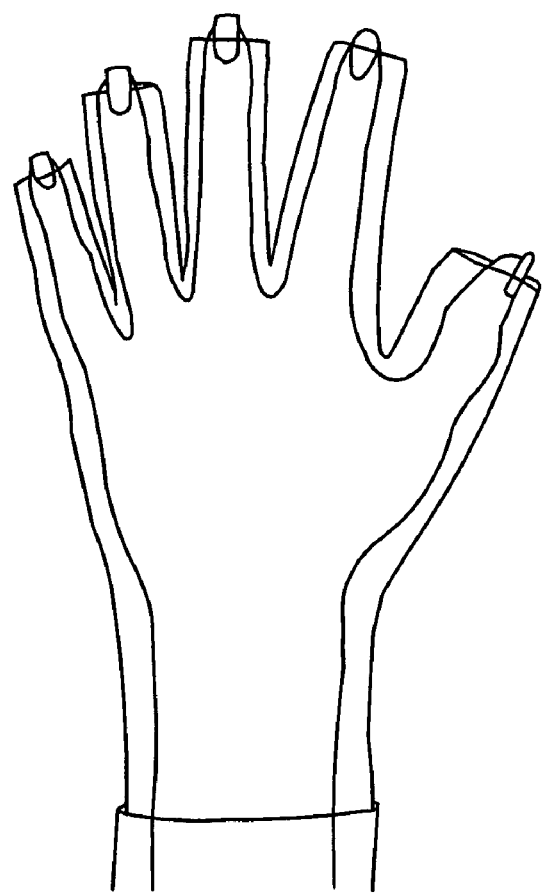
FIG. 22 is a top view of another embodiment of the thermotherapy device according to the present invention in the form of a thermotherapy glove.

FIG. 22 is a specialized embodiment, a thermotherapy glove. One glove fits left or right hand and wrist complex. The glove extends 3" to 4" above the wrist, and is available in a variety of sizes. It uses one VELCRO®-like adjustable strap located around the distal end of the wrist. Another preferred embodiment may employ two (2) VELCRO®-like adjustable straps, one at the distal end of the wrist, as illustrated, and one around the dorsal palmar aspect of the wearer's hand. The fingers of the glove are cut at the distal joint of the fingers in order to check skin or nail discoloration during treatments. The glove also displays a hand in this cut away to view. The embodiment includes separate finger compartments.

Figure 23:
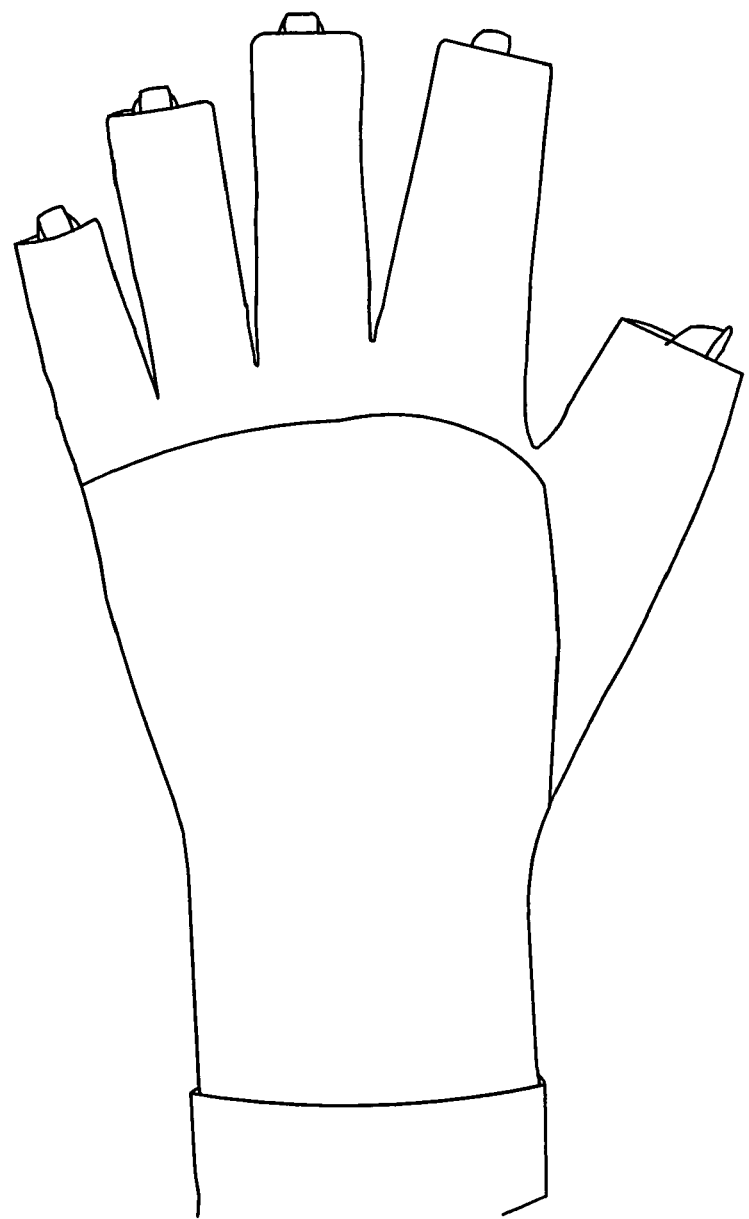
FIG. 23 is a top view of the thermotherapy glove with separate finger compartments.

FIG. 23 is a top view of another preferred embodiment of the thermotherapy glove, with separate finger compartments. This embodiment opens up from the fingers to the wrist, offering another choice for application and removal. The bump (13) system is used throughout the entire interior contact surfaces as well as with the thermotherapy boot. Both marks THERMABUMP® and THERMABOOT® are registered to the inventor of this invention, and inventor has found a substantial market potential for the embodiments of this invention which is in the process of being commercialized.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A non-ambulatory thermotherapy device for contacting and applying hot or cold therapy to a treatment area of a user of the non-ambulatory thermotherapy device, the non-ambulatory thermotherapy device comprising:

at least one pad made of a gel material for contacting the user's treatment area and for undergoing heating or cooling to specific temperatures to apply hot or cold therapy, respectively, to the user's treatment area, the at least one pad having opposite main surfaces and a plurality of bumps extending from one of the main surfaces for increasing a surface contact between the gel material and irregularly shaped contours of the user's treatment area during application of hot or cold therapy to the user's treatment area;

wherein the at least one pad comprises a first pad and the user's treatment area comprises a first part of the user's treatment area, and further comprising a second pad separate and independent from the first pad and made of a gel material for contacting a second part of the user's treatment area and for undergoing heating or cooling to specific temperatures to apply hot or cold therapy, respectively, to the second part of the user's treatment area, the second pad having opposite main surfaces and a plurality of bumps extending from one of the main surfaces for increasing a surface contact between the gel material and irregularly shaped contours of the second part of the user's treatment area during application of hot or cold therapy to the second part of the user's treatment area;

wherein the first and second pads are contained in respective first and second cloth enclosures that house the first and second pads including the corresponding bumps, the first and second cloth enclosures being connected together to form a preselected configuration so that during use of the non-ambulatory thermotherapy device, the first and second pads contact the respective first and second parts of the user's treatment area for application of hot or cold therapy to the first and second parts of the user's treatment area, and further comprising means for adjusting the degree of contact between the bumps of the first and second pads and the corresponding first and second parts of the user's treatment area via the corresponding cloth enclosure; and wherein the preselected configuration of the connected first and second cloth enclosures housing the respective first and second pads is in the shape of a boot having a body formed of the first pad and the first cloth enclosure and a sole formed of the second pad and the second cloth enclosure, and wherein the means for adjusting comprises a strap attachment secured to the body, a pair of strap attachments secured to the sole, an adjustable strap secured to the sole for removable adjustable connection to one of the pair of strap attachments secured to the sole, and adjustable straps secured to the body for removable adjustable connection to the strap attachment secured to the body and the other of the pair of strap attachments secured to the sole, respectively.

2. A non-ambulatory thermotherapy device for contacting and applying hot or cold therapy to a treatment area of a user of the non-ambulatory thermotherapy device, the non-ambulatory thermotherapy device comprising:

at least one pad made of a gel material for contacting the user's treatment area and for undergoing heating or cooling to specific temperatures to apply hot or cold therapy, respectively, to the user's treatment area, the at least one pad having opposite main surfaces and a plurality of bumps extending from one of the main surfaces for increasing a surface contact between the gel material and irregularly shaped contours of the user's treatment area during application of hot or cold therapy to the user's treatment area;

wherein the at least one pad comprises a first pad and the user's treatment area comprises a first part of the user's treatment area, and further comprising a second pad separate and independent from the first pad and made of a gel material for contacting a second part of the user's treatment area and for undergoing heating or cooling to specific temperatures to apply hot or cold therapy, respectively, to the second part of the user's treatment area, the second pad having opposite main surfaces and a plurality of bumps extending from one of the main surfaces for increasing a surface contact between the gel material and irregularly shaped contours of the second part of the user's treatment area during application of hot or cold therapy to the second part of the user's treatment area;

wherein the first and second pads are contained in respective first and second cloth enclosures that house the first and second pads including the corresponding bumps, the first and second cloth enclosures being connected together to form a preselected configuration so that during use of the non-ambulatory thermotherapy device, the first and second pads contact the respective first and second parts of the user's treatment area for application of hot or cold therapy to the first and second parts of the user's treatment area, and further comprising means for adjusting the degree of contact between the bumps of the first and second pads and the corresponding first and second parts of the user's treatment area via the corresponding cloth enclosure;

wherein the preselected configuration of the connected first and second cloth enclosures housing the respective first and second pads is in the shape of a boot having a body formed of the first pad and the first cloth enclosure and a sole formed of the second pad and the second cloth enclosure; and further comprising a first reinforcement scrim attached to one of the main surfaces of the first pad opposite to the other main surface thereof from which the bumps extend for reinforcing the first pad, and a second reinforcement scrim attached to one of the main surfaces of the second pad opposite to the other main surface thereof from which the bumps extend for reinforcing the second pad.

3. A non-ambulatory thermotherapy device for contacting and applying hot or cold therapy to a treatment area of a user of the non-ambulatory thermotherapy device, the non-ambulatory thermotherapy device comprising:

at least one pad made of a gel material for contacting the user's treatment area and for undergoing heating or cooling to specific temperatures to apply hot or cold therapy, respectively, to the user's treatment area, the at least one pad having opposite main surfaces and a plurality of bumps extending from one of the main surfaces for increasing a surface contact between the gel material and irregularly shaped contours of the user's treatment area during application of hot or cold therapy to the user's treatment area;

wherein the at least one pad comprises a first pad and the user's treatment area comprises a first part of the user's treatment area, and further comprising a second pad separate and independent from the first pad and made of a gel material for contacting a second part of the user's treatment area and for undergoing heating or cooling to specific temperatures to apply hot or cold therapy, respectively, to the second part of the user's treatment area, the second pad having opposite main surfaces and a plurality of bumps extending from one of the main surfaces for increasing a surface contact between the gel material and irregularly shaped contours of the second part of the user's treatment area during application of hot or cold therapy to the second part of the user's treatment area;

wherein the first and second pads are contained in respective first and second cloth enclosures that house the first and second pads including the corresponding bumps, the first and second cloth enclosures being connected together to form a preselected configuration so that during use of the non-ambulatory thermotherapy device, the first and second pads contact the respective first and second parts of the user's treatment area for application of hot or cold therapy to the first and second parts of the user's treatment area, and further comprising means for adjusting the degree of contact between the bumps of the first and second pads and the corresponding first and second parts of the user's treatment area via the corresponding cloth enclosure;

wherein the preselected configuration of the connected first and second cloth enclosures housing the respective first and second pads is in the shape of a glove having a first glove piece formed of the first pad and the first cloth enclosure and a second glove piece formed of the second pad and the second cloth enclosure, the connected first and second cloth enclosures forming separate finger compartments for accommodating fingers of a user's hand having the treatment area to which the hot or cold therapy is applied during use of the non-ambulatory thermotherapy device; and further comprising a first reinforcement scrim attached to one of the main surfaces of the first pad opposite to the other main surface thereof from which the bumps extend for reinforcing the first pad, and a second reinforcement scrim attached to one of the main surfaces of the second pad opposite to the other main surface thereof from which the bumps extend for reinforcing the second pad.

4. A non-ambulatory, non-weight bearing thermotherapy boot for contacting and applying hot or cold therapy to a user's foot/ankle complex, the non-ambulatory, non-weight bearing thermotherapy boot comprising:

a pair of pads each made of a gel material for contacting the user's foot/ankle complex and for undergoing heating or cooling to specific temperatures to apply hot or cold therapy, respectively, to the user's foot/ankle complex, each of the pads having opposite main surfaces and a plurality of bumps extending from one of the main surfaces for increasing a surface contact between the gel material and irregularly shaped boney contours of the user's foot/ankle complex during application of hot or cold therapy to the user's foot/ankle complex;

a pair of cloth enclosures housing the respective pair of pads including the corresponding bumps, the cloth enclosures being connected together to form a configuration in the shape of a boot having a body formed of one of the pair of pads and one of the pair of cloth enclosures and a sole formed of the other of the pair of pads and the other of the pair of cloth enclosures; and means for securing the connected cloth enclosures to one another so that the non-ambulatory thermotherapy boot is non-weight bearing during application of hot or cold therapy to the user's foot/ankle complex, and for adjusting the degree of contact between the bumps of the pair of pads and the selective regions of the user's foot/ankle complex during application of hot or cold therapy to the user's foot/ankle complex by the non-ambulatory, non-weight bearing thermotherapy boot, the means for securing and adjusting comprising a single strap attachment secured to the body, a pair of strap attachments secured to the sole, an adjustable strap secured to the sole for removable adjustable connection to one of the pair of strap attachments secured to the sole, and adjustable straps secured to the body for removable adjustable connection to the single strap attachment secured to the body and the other of the pair of strap attachments secured to the sole, respectively.

5. A non-ambulatory, non-weight bearing thermotherapy boot according to claim 4; further comprising a first reinforcement scrim attached to one of the main surfaces of one of the pair of pads opposite to the other main surface thereof from which the bumps extend for reinforcing the one pad, and a second reinforcement scrim attached to one of the main surfaces of the other of the pair of pads opposite to the other main surface thereof from which the bumps extend for reinforcing the other pad.

* * * * *